United States Patent [19]

Nangia et al.

[11] Patent Number: 5,196,190
[45] Date of Patent: Mar. 23, 1993

[54] SYNTHETIC SKIN SUBSTITUTES

[75] Inventors: Avinash Nangia, San Francisco, Calif.; Cheung-Tak Hung, Pine Hill, New Zealand

[73] Assignee: Zenith Technology Corporation, Limited, Dunedin, New Zealand

[21] Appl. No.: 607,128

[22] Filed: Oct. 3, 1990

[51] Int. Cl.$^5$ .................. A61L 15/06; A61K 31/74
[52] U.S. Cl. .................. 424/78.06; 424/78.32; 424/78.07; 424/447; 514/772.5; 514/777; 514/780; 514/781; 514/782; 602/48; 602/51; 602/52; 602/56
[58] Field of Search .............. 424/78, 447, 78.06, 424/78.32; 525/54.2, 54.22, 54.21; 514/772.5, 777, 780, 781, 782

[56] References Cited

U.S. PATENT DOCUMENTS

| | | | |
|---|---|---|---|
| 3,376,282 | 4/1968 | Schweiger et al. | 525/54.2 |
| 3,645,939 | 2/1972 | Gaylord | 525/54.23 |
| 3,969,498 | 7/1976 | Catania et al. | 424/28 |
| 4,330,441 | 5/1982 | Bohmer et al. | 525/54.21 |
| 4,393,080 | 7/1983 | Pawelchak et al. | 428/355 |
| 4,538,603 | 9/1985 | Pawelchak et al. | 424/447 |
| 4,587,284 | 5/1986 | Luissi et al. | 524/17 |
| 4,777,046 | 10/1988 | Iwakura et al. | 424/447 |
| 4,929,577 | 5/1990 | Cornell | 424/447 |

FOREIGN PATENT DOCUMENTS

| | | |
|---|---|---|
| 0130061 | 1/1985 | European Pat. Off. |
| 0165074 | 12/1985 | European Pat. Off. |
| 0190814 | 8/1986 | European Pat. Off. |
| 198344 | 7/1984 | New Zealand |
| WO86/02095 | 4/1986 | PCT Int'l Appl. |
| 1521171 | 8/1978 | United Kingdom |
| 2036042A | 6/1980 | United Kingdom |
| 1594389 | 1/1981 | United Kingdom |
| 2099704A | 12/1982 | United Kingdom |

OTHER PUBLICATIONS

Nangia et al "Preclinical Evaluation ..." Burns (1990) 16(5), pp. 358-367.
Nangia et al "Design of a new ..." Burns (1989) 15 (6), pp. 385-388.
Nangia et al "Laboratory Evaluation ..." Burns, (1990) 16(5) pp. 368-372.
Chemical Abstracts, vol. 94 No. 22, Jun. 1 1981, p. 377, Abstract #180641g Wang et al.

Primary Examiner—Thurman K. Page
Assistant Examiner—Peter F. Kulkosky
Attorney, Agent, or Firm—Nixon & Vanderhye

[57] ABSTRACT

Membranes suitable for use as wound dressings and in particular as synthetic skin substitutes are disclosed. The membranes consist of a natural or synthetic polymer, a non-gellable polysaccharide and a cross-linking agent.

The membranes of the invention may contain one or more additional components selected from water-loss control agents, emulsifying agents and plasticizers. An internal reinforcing material may also be provided to supplement the inherent mechanical strength of the membrane.

Methods of forming such membranes are also disclosed.

19 Claims, 1 Drawing Sheet

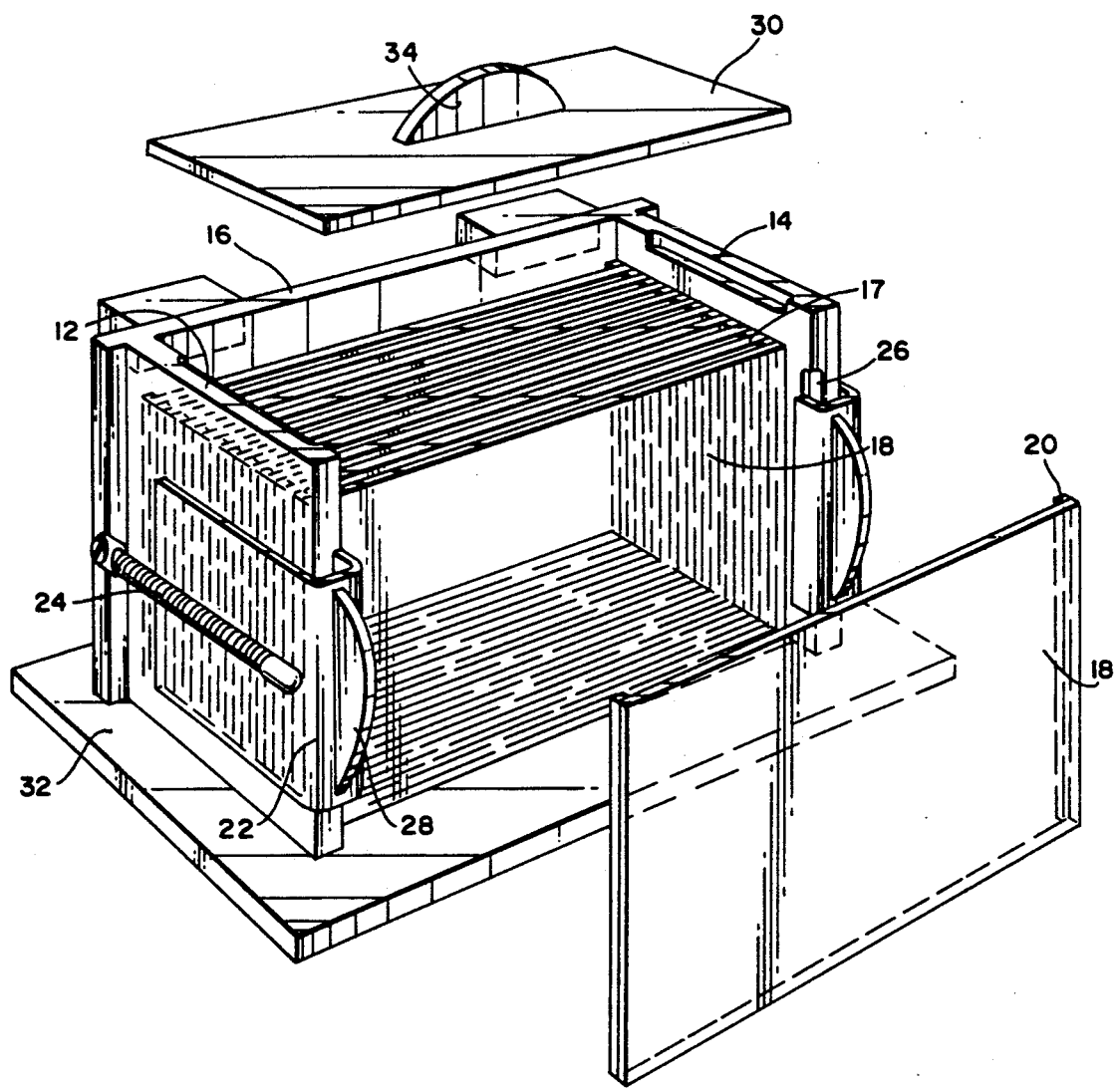

SYNTHETIC SKIN SUBSTITUTES

BACKGROUND OF THE INVENTION

The outer layer of skin surrounding the body performs an important protective function as a barrier to infection and as a means of regulating the exchange of heat, fluid and gas between the body and external environment. Where the skin is removed or damaged by being abraded, burnt or lacerated, this protective function is diminished. Such areas of damaged skin are therefore conventionally protected by the application of a wound dressing which serves as a skin substitute.

Examples of wound dressings which have been developed are hydrocolloid dressings. UK Patent Number 1471013 and Catania et al U.S. Pat. No. 3,969,498 describe hydrocolloid dressings which are plasma soluble, which form an artificial eschar with the moist elements at the wound site, and which gradually dissolve to release medicaments. These dressings comprise a hydrophilic foam of dextran polymer which can be applied without inunction, is non-irritating to the lesion and is easily removed.

Known hydrocolloid dressings in general, and the Catania dressings in particular, are however subject to a number of drawbacks. The major disadvantages of these dressings are that they disintegrate in the presence of excess fluid at the wound site and that they have little if any control over water loss from the wound. This latter disadvantage is particularly important as excess water loss from a wound will cause an increase in heat loss from the body as a whole, potentially leading to hypermetabolism.

In addition, such hydrocolloid dressings as are known require frequent dressing changes. This is especially true of the Catania dressing due to the dissolution of the dextran polymer at the wound site by the fluid lost through the wound in the exudative stage.

New Zealand Patent Specification Number 198344 discloses a bandage which contains a medicament that is administered topically to the skin of a patient. The bandage disclosed comprises a backing element and a self-adhesive matrix, which matrix in turn comprises a solid phase and a liquid phase with the medicament being molecularly dispersed in the matrix. While the solid phase of the matrix can comprise synthetic polymers and natural gums, no teaching is provided of a synthetic skin substitute which can consist of only a natural or synthetic polymer, a non-gellable polysaccharide and a cross-linking agent.

It is an object of the present invention to go some way towards overcoming the above disadvantages or at least to provide the public with a useful choice.

SUMMARY OF THE INVENTION

Accordingly, in one aspect the present invention can broadly be said to consist in membrane suitable for use as a synthetic skin substitute, said membrane consisting of a natural or synthetic polymer, a non-gellable polysaccharide, and a cross-linking agent.

In one embodiment, the natural or synthetic polymer is a dextran polymer which is cross-linked to the non-gellable polysaccharide by a cross-linking agent.

In a particularly preferred embodiment, the natural or synthetic polymer is polyacrylamide comprising acrylamide monomers cross-linked into a cross-linked mass by said cross-linking agent, the non-gellable polysaccharide being incorporated into said mass.

Conveniently, the non-gellable polysaccharide is a non-gellable galactomannan.

As used herein, the term "non-gellable" means a substance which has no gelling properties in itself, i.e. which does not undergo conformational transition during heating and cooling.

In preferred embodiments, the membrane further includes one or more of a water loss control agent, a plasticizer and an emulsifying agent.

The membrane optionally also includes a reinforcing material, preferably perforated, in order to increase its overall strength. In a further aspect, the invention may be said to consist in a method of preparing a membrane comprising the steps of:

dispersing a non-gellable polysaccharide in water;
adding to said dispersion a natural or synthetic monomeric or polymeric material, a cross-linking agent and a cross-linking catalyst, and mixing as appropriate;
adding the mixture thus formed to a membrane casting apparatus; and
allowing said mixture to remain in said apparatus under appropriate conditions and for a sufficient time for said membrane to form.

Where the natural or synthetic material is acrylamide, the mixture is maintained in the membrane casting apparatus in the substantial absence of oxygen and at a temperature below 10° C.

Conveniently, said dispersion includes a hydration control agent such as isopropyl alcohol (propan-2-ol) to enhance the formation of a coherent close knit mass of non-gellable polysaccharide.

It will be appreciated that the monomeric or polymeric material, the cross-linking agent and the cross-linking catalyst can be added to the dispersion together or separately.

Conveniently, the method includes the preliminary step of forming a solution comprising the monomeric or polymeric material, the cross-linking agent and the cross-linking catalyst and adding the solution to the dispersion. Alternatively, the method may include the steps of forming a solution comprising the monomeric or polymeric material and the cross-linking agent, adding the solution to the dispersion and conducting a first mixing step, then adding the cross-linking catalyst and conducting a second mixing step prior to adding the mixture to the membrane casting apparatus.

Where the membrane is to include a perforated reinforcing material, the material is appropriately positioned within the casting apparatus prior to the addition of the mixture.

Also described herein is a membrane casting apparatus including:

first and second framing members, said framing members being positionable opposite and substantially parallel to each other;
a plurality of partitioning members, said partitioning members being positionable spaced apart between said framing members and substantially parallel to each other such that a separate open-ended compartment is formed between the framing members and adjacent partitioning members;
means capable of spacing said partitioning members apart;
means capable of retaining said partitioning members in position;

a first closure member capable of covering one open end of each compartment; and
a second closure member capable of covering the other open end of each compartment;
the arrangement being such that when assembled, each said compartment is closed and the ingress of air thereinto is resisted.

In some embodiments, a single structure can function as both the spacing means and the retaining means.

In a preferred embodiment, the apparatus includes a substantially rectangular backing member, said backing member having attached thereto said first and second framing members at opposite ends thereof. In this embodiment the positioning means conveniently comprises means cooperable with the partitioning members and which bias the partitioning members toward the backing member, and the spacing means comprises spacing elements provided on the same side but at or towards the opposite ends of each partitioning member which elements in use abut against the adjacent partitioning member.

In still a further aspect, the invention consists in a method of treating burns, donor sites, excised wounds, ulcers or dermal abrasions comprising applying a membrane as defined above to said burn, donor site, wound, ulcer or abrasion.

BRIEF DESCRIPTION OF THE DRAWING

Although the invention has been broadly described above, it will be understood that it is not limited to the foregoing but also consists in embodiments of which the following description gives examples. In addition, aspects of the invention will be more fully understood by having reference to the drawing accompanying the specification showing the preferred form of the membrane casting apparatus.

DETAILED DESCRIPTION OF THE INVENTION

In one embodiment, the invention comprises a wound dressing in the form of a flexible membrane. The membrane is particularly suited for use as a skin substitute where the skin of a patient has been removed or damaged by for example abrasion or burning.

In the broadest aspect of this embodiment of the invention, the membrane includes a natural or synthetic polymer and a non-gellable polysaccharide. Although the following description is provided in relation to membranes in which polyacrylamide and dextran are the natural or synthetic polymers, it will be appreciated that the invention is not limited thereto.

In the presently preferred formulation of the invention where the natural or synthetic polymer is polyacrylamide, the acrylamide monomers are cross-linked with a cross-linking agent to form a thermally stable three dimensional coherent mass. The presently preferred cross-linking agent is NNN'N'-methylenebisacrylamide although other appropriate cross-linking agents such as bisacrylylcystamine and diallyltartardiamide may also be used.

The final and most critical component of the preferred membrane is a non-gellable polysaccharide, preferably a galactomannan macromolecule, which is incorporated within the polyacrylamide cross-linked mass. It has surprisingly been found by the inventors that the incorporation of a non-gellable polysaccharide results in a membrane which overcomes most if not all of the problems with prior art wound dressings while at the same time being simple and relatively inexpensive to produce. In particular, the incorporation of this component avoids the problem of shrinkage and fragility attendant upon the membrane drying, imparts mechanical strength to the membrane and reduces the pore size of the inherent membrane, thereby making it impermeable to microorganisms. Conveniently, the non-gellable polysaccharide is a non-gellable galactomannan macromolecule such as guar gum but other macromolecules such as lucerne, fenugreek, honey locust bean gum, white clover bean gum and carob locust bean gum may also be used.

Where the natural or synthetic polymer is dextran, the dextran is cross-linked to the non-gellable polysaccharide by a cross-linking agent to form a stable coherent mass. It is preferred that the molecular weight of the dextran polymer be between 50,000 and 500,000, most preferably between 75,000 and 100,000.

In this formulation, the non-gellable polysaccharide and cross-linking agent are preferably those described above.

In addition to the essential components described above, in its preferred form the membrane contains a number of further components. In a particularly preferred embodiment, the membrane incorporates a water loss control agent such as a phospholipid. Phospholipid is an essential water holding lipid of human skin and therefore its inclusion as a component of the membrane will provide an additional barrier to both heat and water loss from the wound, thus aiding in the restoration of normal metabolism. Variation in the amount of phospholipid incorporated into the membrane adjusts the rate of water vapour transport of the membrane by effecting the water permeability of the strucutre. By way of example incorporation of 10% W/W of the phospholipid, L-α-phosphatidylcholine into the membrane allows water permeability of approximately 1400–2200 grams/$m^2$/24 hours, which is well within the range of 2000–2500 gram/$m^2$/24 hours required for burn coverings. Inclusion of a phospholipid component in the membrane also has an additional advantage in that the dressing is more adherent to both intact and abraded skin when a phospholipid is present.

As indicated above, the presently preferred water loss control agent is L-α-phosphatidylcholine. However, substances other than phospholipids which control water loss such as glycolipids, ceramides, free fatty acids, cholesterol, triglycerides, sterylesters, cholesteryl sulfate, linoleic ethyl ester and silicone oil may also be used.

The use of phospholipid as the water loss control agent also has other advantages. In particular, where it si desired to use the membrane as a sustained topical drug delivery service, the phospholipid may be incorporated in the form of lipid vesicle liposomes containing the desired drug. By way of example, various antimicrobial compounds, germicides, steroids, anaesthetics, chemotactic agents, angiogenic agents and epidermal growth factors may be incorporated in the membrane of the present invention in this manner.

A further component which it is desirable to incorporate into the membrane of the invention is an emulsifying agent. Inclusion of this component enhances the emulsification of the water loss control agent component into the membrane. The presently preferred emulsifier is the anionic surfactant sodium lauryl sulphate but other anionic surfactants and non-ionic surfactants such as tweens, triton-X and pluronics may also be used.

Where the membrane is to be used as a skin substitute in an area which requires a particular degree of elasticity, a plasticiser such as glycerol may be incorporated into the composition as an additional component. Glycerol may be substituted by other known plasticisers such as sorbitol, propylene glycols, PEG-400, PEG-75-lanolin oil, diethylene glycol, acetylated lanolin or mixtures thereof.

The membrane optionally further includes a reinforcing material to enhance the strength of the product. The reinforcing material is preferably in the form of a sheet or net of material, the shape and dimensions of which correspond substantially to those of the membrane to be coextensive therewith. It is further preferred that the material be incorporated having a membrane layer on either side thereof. In this embodiment, the reinforcing material is perforated to allow both sides of the membrane to bond together through the perforations and to allow fluid communication between both sides of the membrane. This latter feature is important to maximise the absorptive capacity of the membrane for wound exudate.

The presently preferred reinforcing material is a perforated polyester material. However, any of those reinforcing materials known in the art which would be suitable for the purpose could be used. By way of illustration, polyethylene, polypropylene, PVC, polystyrene, PTFE, celluslose derivatives, polybutadiene, polylactide, polyurethane, polypeptides, poly (E-caprolactone), nylon, keratin, collagen, chitin, chitosen, Styrene-butadiene copolymers and derivatives thereof can also be used, either alone or in a mixture.

The membranes according to the present invention may be prepared in accordance with the following process.

The first step of the process comprises the formation of a dispersion of the non-gellable polysaccharide component of the membrane in water. This dispersion may advantageously also include a hydration control agent for the polysaccharide to enhance the formation of a coherent, close-knit mass. In addition, where such a hydration control agent is present, the polysaccharide macromolecule can be used at higher concentrations. An example of suitable hydration control agent is isopropyl alcohol (propan-2-ol).

The second step of the process involves the addition of the remaining components of the membrane (the monomeric or polymeric material and the cross-linking agent) together with a cross-linking catalyst to the dispersion. The cross-linking catalyst is added to catalyse the cross-linking reaction involved in the formation of the membrane. Examples of suitable catalysts are NNN'N'-tetramethylene diamine and ammonium persulfate.

All of the components are then mixed together and homogenized before being poured into a membrane casting apparatus. Although it is preferred that the membrane casting apparatus is that described hereinafter as an aspect of the invention, this is not critical. Instead, the casting apparatus may be any of those known in the art suitable for this purpose. This is particularly the case where the membrane being formed includes dextran which does not require the controlled polymerisation conditions set out below necessary to form the polyacrylamide membrane.

Where the membrane being formed includes acrylamide monomers cross-linked to form polyacrylamide, the mixture is then maintained in the absence of oxygen at a temperature of less than 10° C. for a period of time sufficient for the membrane to form. Conveniently, the mixture is maintained at a temperature between 4° and 10° C. during the polymerisation process.

In contrast, where the membrane to be formed includes dextran the polymerisation mixture is maintained at room temperature and is open to air.

The monomeric or polymeric material, the cross-linking agent and the cross-linking catalyst can be added to the dispersion either together or separately. Where each of the above components are to be added to the dispersion together, a solution containing them is formed which is then added to the dispersion. The solution and the dispersion are then mixed to provide the mixture to be added to the membrane casting apparatus. In other embodiments of the method, the monomeric or polymeric material and the cross-linking agent are added to the dispersion separately from the cross-linking catalyst. In this embodiment, a solution comprising the monomeric or polymeric material and the cross-linking agent is added to the dispersion and a first mixing step conducted. The cross-linking catalyst is then added, a second mixing step conducted, and the resulting mixture poured into the membrane casting apparatus.

Where the membrane to be formed is also to include a water loss control agent and/or an emulsifying agent as components, these are also added to the dispersion prior to the mixing step. Again, these preferred components can be added either separately or together with the other components.

Where the membrane is to include a reinforcing material, this material is positioned with each compartment of the membrane casting apparatus prior to the addition of the polymerisation mixture.

If desires, the incorporation of the plasticiser into the membrane is achieved by immersing the membrane formed as above into an aqueous solution of the plasticiser. The concentration of the plasticiser and duration of the membrane immersion in the aqueous solution will depend on the degree of elasticity desired for that particular membrane.

The present invention will be more clearly understood by having reference to the following non-limiting examples.

EXAMPLE 1

Formation of a membrane including acrylamide 0.8 g of purified guar-gum (molecular weight of 2.2 million) was dispersed in 20 ml of a mixture containing 2 ml of isopropyl alcohol (propan-2-ol) and 18 ml distilled water to form a dispersion. 7 g of monomeric acrylamide and 160 mg of NN'-methylenebisacrylamide were dissolved in 20 ml of distilled water to form a solution. 0.8 g of L-$\alpha$-phosphatidylcholine was solubilised in 20 ml of distilled water using 50 mg of sodium lauryl sulfate using an ultrasonic probe to form a second dispersion.

The solution and the second dispersion were then added to the first dispersion and homogenised for about five minutes. 100 $\mu$l of NNN'N'-tetramethylene-diamine and 100 mg of ammonium persulfate were then added to and mixed into the mixture.

The resulting mixture was then poured into a membrane casting apparatus as is described below and allowed to cross-link in the absence of air and at a temperature of from 4° to 10° C. for period of time sufficient to allow the membrane to form.

The membrane was then removed from the casting apparatus and immersed in normal saline to remove the unreacted substances, followed by immersion in a 5% w/w aqueous glycerol solution for 5 hours and then dried at 50° C.

When dry, the membrane was sterilized. The technique used was exposure to ethylene oxide but other techniques such as autoclaving or radiation are equally applicable.

EXAMPLE 2

Formation of a membrane including dextran.

0.3 g of purified guar gum (molecular weight 2.2 million) was dispersed in 20 ml of distilled water. 3 g of dextran (molecular weight 81,500) was then mixed with 50 mg of sodium lauryl sulphate, 3 ml epichlorohydrin, 300 mg L-α-phosphatidylcholine and 20 ml of 1M sodium hydroxide to form a solution.

The solution was then added to the dispersion and homogenised for five minutes. The mixture thus formed was poured into the membrane casting apparatus and the apparatus maintained at 40° C. for 24 hours to remove The membrane casting apparatus used in this case consisted of a glass ring of approximately 70 mm in diameter, with a Whatmen ® Sealing Film or an unsintered Teflon ® film securely fastened on one side using a rubber band.

When the polymerization reaction was completed, the membrane was easily removed from this assembly by unfastening the base film and soaking the remaining assembly in water for approximately 20 minutes.

The membrane was then successively rinsed with distilled water, 0.1M hydrochloric acid and again distilled water to remove any unreacted substances, immersed in a 5% W/W aqueous glycerol solution for four hours and then dried at 45° C.

When dry, the membrane was sterilized by autoclaving.

The above examples are merely provided as an indication of the procedure to be followed in preparing the membranes according to the invention. In particular, it will be appreciated by those persons skilled in the art that the amount of each component will vary depending on the size of the membrane to be formed and on the particular requirements of the site to which it is to be applied. Further, the membrane can be made in any size by appropriate modification of the membrane casting apparatus.

Also provided herein is a membrane casting apparatus. The apparatus includes first and second framing members which are positionable opposite and substantially parallel to each other.

The apparatus further includes a plurality of partitioning members which are in turn positionable between the first and second framing members. The partitioning members are spaced apart and substantially parallel to each other. In this way, a separate open-ended compartment is formed between the first and second framing members and each pair of adjacent partitioning members.

The apparatus also includes means by which the partitioning members can be spaced apart. The spacing means can be provided as a part of either the partitioning members themselves or the framing members. As a part of the framing members the spacing is achieved by provision of a series of slots in the surfaces of the framing members which face each other, the slots being cooperable with the distal ends of the partitioning members. In this embodiment the slots and ends of the partitioning members cooperable with the slots are preferably shaped such that the partitioning members are retained in position. In this way, the partitioning members and the framing members can be arranged into a structure which provides a series of open-ended compartments, but which is easily and quickly disassemblable.

In the presently prefered embodiment, the spacing is achieved by spacing elements attached to the partitioning members themselves. Conveniently, the spacing elements are of substantially the same dimensions and are attached to opposite ends of the partitioning members. In this way, the spacing between the partitioning members can be varied as desired, which in turn varies both the volume of the compartment formed and the thickness of membrane being cast.

The apparatus also includes means by which the partitioning members can be retained in position. Where the spacing of the partitioning members is achieved by the provision of slots in the framing members, the positioning means comprises the slots themselves appropriately shaped to retain the ends of the partitioning members in place. In the alternative and preferred embodiment, the positioning means comprises means cooperable with the partitioning members and which bias the partitioning members towards a fixed element of the apparatus. This fixed element may comprise either the final partitioning member of the series or a backing member positioned parallel to the partitioning members and which has the framing members positioned at opposite ends thereof.

The casting apparatus is completed by the provision of first and second closure members which close or cover the open ends of the compartments formed between the partitioning and framing members. In this way when all the components of the apparatus are assembled together, a plurality of closed compartments are provided into which the ingress of air is resisted.

The components of the casting apparatus can be formed from any material which is not affected by polymerisation reaction involved in the formation of the membrane. However, a transparent plastics or glass material is preferred to allow the polymerisation process to be observed without opening the compartments to air.

The most preferred construction of the membrane casting apparatus will now be described with reference to the accompanying drawing.

As shown, first and second framing members 12, 14 are provided at opposite ends of a backing member 16. Between the framing members 12 and 14 are positioned a plurality of partitioning members 18 which are substantially parallel to backing member 16. Partitioning members 18 are spaced apart from each other by the provision of spacing elements 20 at opposite ends of each partitioning member 18. A plurality of separate open-ended compartments 17 are thus formed between the partitioning members.

As shown, these spacing elements 20 abut directly against the adjacent partitioning member 18 and set the distance between each pair of partitioning members. Alternatively, where a reinforcing material is to be included in the membrane, the spacing elements 20 abut against secondary spacing elements (not shown) projecting from the surface of the adjacent partitioning member 18. The provision of the secondary spacing elements allows the reinforcing material to be fixed in a position within each compartment by being held between the abutting suraces of the respective spacing elements.

The preferred apparatus also includes paired positioning means which bias the partitioning member 18 toward backing member 16. As shown each positioning means comprises a portion 22 for contacting the outermost partitioning member and a spring 24 attached at one end to the contact portion 22 and at the other end to backing member 16. At the end of framing members 12 and 14 remote from backing member 16 there is provided a ledge 26 onto which contact portion 22 can be positioned out of engagement with the partitioning members 18 to allow for easy removal of the partitioning members. A gripping element 28 is also attached to each contact portion 22 to facilitate the movement of the contact portion to its rest postion on ledge 26.

The apparatus further includes closure members in the form of a lid 30 and a base 32 which serve to cover the top and bottom openings of each compartment 17. Lid 30 is also provided with a gripping element 34 to allow easy removal.

In operation, the components of the apparatus as shown are assembled. Where the membrane is to include a reinforcing material, this is positioned in each compartment 17 and held in position between the spacing elements. The mixture formed in accordance with the process of the invention is added to the compartments 17 and the lid 30 positioned to close each compartment.

Following the formation of the membrane, the lid 30 is removed, the contact portion 22 is moved out of engagement with the outermost partitioning member and the partitioning members 18 removed. The formed membranes are then separated from the partitioning members for further treatment.

The membranes of the invention of the preferred polyacrylamide formulation have been subjected to a number of tests. The results of these tests are as follows.

The polyacrylamide membranes of the present invention formed as above are permeable to water vapour. The water vapour permeation transmission was determined on excised skin wounds of rats covered with a membrane. An EVAPORIMETER (Servomed AB) was used to find the water vapour transmission. The data obtained shows that the permeability of membrane is in the range of 1400-2500 grams/m$^2$/24 hours. The membranes therefore have water vapour transport characteristics sufficient to keep the underlying tissues moist without fluid pooling or dehydration, both of which conditions retard wound healing.

The oxygen permeability of the membrane was measured by using a specially designed oxygen permeability cell using an oxygen electrode. The data obtained shows that the dissolved oxygen permeability of the membrane is int he range of $1.4-2.40 \times 10^{-9}$ [cm$^3$.(STP).cm/cm.$^2$sec.cm.Hg]. Therefore the membrane is highly permeable to oxygen which will promote wound healing.

The polyacrylamide membranes of the present invention also have a high absorption capacity for exudate and tissue secretions at the wound site. When the membrane was immersed in distilled water at ambient temperature of 22° C., the rate of water absorption was 900% in 24 hours, without losing durability. The present membranes are therefore highly suitable for use in treating wounds which produce large amounts of exudate.

The membranes of the present invention are also elastic, self-supporting and flexible. Tensile properties of the polyacrylamide membranes were studied according to ASTM D882-81, 1981 at 65% relative humidity (21° C.). The elongation at the breaking point of the membrane is 400-750%, with a tensile strength of 2-3 MPa and an initial modulus of 0.5-0.9 MPa. It will be clear to those persons skilled in the art that the elasticity of the membrane can be adjusted by altering the concentration of plasticizer and components of the membrane, allowing the membrane to be stretched over joints without causing a shear stress that will break the adherence between the dressing and the wound surface.

In order to demonstrate the effectiveness of the membrane according to the invention as a skin substitute, the following clinical experiments were performed.

EXPERIMENT 1

The objective of this experiment was to evaluate the effectiveness of the membrane of the invention (SSS) in the management of excised skin wound in the rats. Its effectiveness has been compared with two marketed products Geliperm Dry (Geistlich Pharma) and Bioclusive (Johnson and Johnson) used for the same purpose.

Experimentation

Sprague-Dawley rats weighing 200-250 gms were anaesthetised by an intraperitoneal injection of pentobarbital and shaved with a clipper. A 4×4 cm area, about 15% of the rat skin, was excised from the dorsal surface with a Reese Drum Dermatome. Histological studies of the skin sections revealed that it was a split thickness injury covering epidermis and most of the dermis. A total of 20 rats were used in the study. Three groups comprising of five randomly selected rats were applied with SSS or Bioclusive or Geliperm Dry and the remaining five rats used as controls with air exposure. In the case of SSS and Geliperm, the membranes were fixed to the wound site with the help of an adhesive tape.

All the animals were observed daily for the evaporative water loss through the membranes, appearance of the wound and the rate of healing.

Results

SSS adhered uniformly onto the wound surface and absorbed exudate from the wound. SSS also appeared to stop bleeding at the wound site and acted as a haemostatic agent. Bioclusive, due to its thin and flexible nature also conformed well to the wound surface. However, it did not absorb the exudate from the wound. Geliperm Dry did not adhere uniformly to the wound side and air pockets were observed between the wound and the dressing. In addition, the membrane showed mimimal exudate absorbing capacity.

When the animals were inspected on day 3 post operation, all rats with Bioclusive showed evidence of pooling of excess exudate and maceration of the wound. The exudate was shown to be contaminated with *Pseudomonas seruginosa* and *Staphylococcus aureus*. Rats with Geliperm Dry showed no adherence to the wound. As it did not protect the wound from desiccation, a thick crust formation on the wound surface was observed. Animals treated with SSS showed uniform adherence to the wound, without fluid accumulation and with no infection. On day 8 post-operation the animals were examined for their degree of epithelialisation at the wound site and the results are presented in Table 1.

TABLE 1

| Treatment | Percentage of wound area re-epithelialised at day 8 of post-operation |
|---|---|
| Air exposed | 50 |
| Bioclusive | 78 |
| Geliperm Dry | 60 |
| SSS | 100 |

As seen from Table 1, animals treated with SSS showed complete wound healing. The entire area also showed uniform growth of hair. Treatment with Bioclusive was quite impressive with an average of 78% of area smoothly re-epithelialised but without any evidence of hair growth. Surface culture showed the presence of infection but it was less that that observed at 3 day post-injury. Those treated with Geliperm Dry showed an average of 60% wound reduction, but crust formation was clearly evident.

EXPERIMENT 2

A clinical report of the usefulness of 'SSS' on scald burns

A young male aged sixteen sustained a scald burn injury to his leg due to the bursting of a hot water bottle. The patient was first inspected two days post-burn and burn injury ranged from superficial to full thickness with oedema and inflammation. Before the application of SSS, necrotic tissues and blisters were debrided, the wound was cleaned with Savlon solution and then rinsed with normal saline. SSS was applied to the area only with full-thickness burns and held in place with a gauze dressing.

At the time of the first follow up visit, three days post-burn, SSS was found uniformly adhering to the wound. The wound was clean and without any sign of exudate accumulation, infection or inflammation. Though the same dressing could have been applied again, it was replaced with a fresh sheet of SSS and wrapped with gauze.

On six days post-burn (4th day post-treatment), epithelialisation had already started and wound size reduced. At inspection on ten days post-burn, the wound was completely healed. As the re-epithelialisation was complete, SSS began to separate out from the wound surface. During the course of treatment, the patient resumed his daily activities and experienced minimal inconvenience.

EXPERIMENT 3

A young female aged five was severely burned as her clothes caught fire. Forty percent of her body surface was involved mainly localised on the trunk and all were deep dermal burns.

Debridement and split thickness skin graft on the back was performed on day 12 following injury. A skin graft was taken from the back of right thigh. SSS was applied both on the donor and recipient areas.

The wounds were examined on day 2 following application of SSS. Marked submembrane collection was detected in both sites (culture of the effusion yielded Pseudomonas). The wounds were thoroughly cleaned with antiseptics. Fresh SSS was applied on the donor sites.

On day 5 post-application of SSS, three quarters of the graft had taken. The dressing on the donor sites was kept intact till day 9 at which time 85% of the wound wa epithelised.

Subsequently, skin grafting was performed on the anterior chest and abdominal walls of the patient. Split thickness skin grafts were taken from both the legs and buttock of the patient. SSS was applied to the donor site.

Dressings on the donor sites were changed because the effusion soaked through the dressings. Fresh SSS was applied and was then kept intact for another seven days. The result was a complete epithelization on the donor areas.

EXPERIMENT 4

A young male aged 11 sustained 10% superficial burn injuries on the back after scalding by hot water.

SSS was applied after the wound was cleaned with Savlon. The SSS was changed on day 2 after application because of marked submembrane collection. The dressings were replaced and remained dry until removal after 7 days. At the time of removal, complete epithelization of the wound has occurred.

Minimal scarring of the patient was detectable three months after healing.

EXPERIMENT 5

A male patient aged 28 sustained deep dermal burn injuries to the middle and ring fingers of right hand due to spillage of hot tar.

The wound was initially treated with topical antibiotics because of marked contaminations. SSS was applied 10 days after injury and the wound examined every two days subsequently. No further dressing was necessary as minimal effusion was detected.

The wound was found to be completely epithelised beneath the SSS on day 7 following application.

Minimal stiffness of the fingers was detectable two months later.

Accordingly the membranes of the present invention possess numerous advantages over those hydrocolloid or hydrogel wound dressings previously known. The present membranes will not dissolve in water and therefore require less frequent dressing changes. This results in significant cost savings and also enhances the wound healing processes by minimising disturbances of the wound.

The membranes of the present invention can be applied to the wound site in various forms. They can be applied to the wound site either as a wet or dry membrane. In the former cases, the membrane can be soaked in saline solution for few seconds before use. They can also be used in dry powder, wet granules or paste form. The latter form is most useful for deep cavities or exudative lesions such as decubitus and venous ulcers.

In addition to the above, the membranes of the invention adhere to any moist surface rapidly and are also strong enough to resist shear stresses. The adherence is uniform and therefore eliminates the fluid filled pockets where bacteria may proliferate as a result of non-adherence.

Where, as is preferred, the membranes incorporate a phospholipid, it is also possible to regulate the water vapour transport of the membrane and the thereby decrease the amount of water lost from the wound. This phospholipid component may also be incorporated int he form of lipid vesicle liposomes containing drugs to be administered topically. In this form, the resistance to dissolution also increases the efficiency of the present membrane as a delivery system for topical therapy as compared to those dressings known. By way of example the serated dextran dry foam described by Catania et al in U.S. Pat. No. 3,969,498 dissolves in water in thirty seconds or less, thus releasing the incorporated drug immediately at the open wound site. In contrast, the membranes of the present invention release the drug slowly over a prolonged period of time, thus eliminating the hazards of dose dumping.

The membranes are also impermeable to microorganisms and accordingly assists wound healing by keeping the wound clean.

Where the membranes incorporate a perforated reinforcing material, the overall strength of the membranes is increased, together with their conformability. This latter feature in particular allows the membranes to be moulded to fit the surface to be covered.

Other advantages of the membranes reside in their transparent nature, allowing wound inspection without removal, and in that they are non-toxic, non-allergenic, antiseptic, easy to apply and remove without inunction, allow gaseous exchange, provide thermal insulation for the wound and are relatively inexpensive.

Thus, in accordance with the present invention there are provided membranes particularly suitable for use as synthetic skin substitutes. To those persons skilled in the art the invention will have obvious utility as a short and long term skin substitute for second and third degree burns, excised wounds, donor sites, ulcers and dermal abrasions.

It will be appreciated by those persons skilled in the art that the above description is provided by way of example only and that it should not be construed as a limitation on the scope of invention to which the applicants are entitled.

What is claimed is:

1. A membrane suitable for use as a synthetic skin substitute consisting essentially of a polyacrylamide network and a non-gellable polysaccharide dispersed evenly throughout said network, wherein said polymeric polyacrylamide network comprises acrylamide monomers cross-linked together by a cross-linking agent and wherein the membrane has a water absorptive capacity greater than of a membrane which includes an amount of a gellable polysaccharide in substitution for the same amount of non-gellable polysaccharide, but which is otherwise the same.

2. A membrane according to claim 1, wherein the non-gellable polysaccharide is a non-gellable galactomannan.

3. A membrane according to claim 2, wherein the non-gellable galactomannan is guar gum.

4. A membrane according to claim 2, wherein the non-gellable galactomannan is selected from honey locust bean gum, white clover bean gum and carob locust bean gum.

5. A membrane according to claim 1, wherein the cross-linking agent is NN'-methylenebisacrylamide.

6. A membrane according to claim 1, wherein the cross-linking gent is selected from bisacrylylcystamine and diallyltartar diamide.

7. A membrane according to claim 1, further including a water-loss control agent.

8. A membrane according to claim 7, wherein the water loss control agent is a phospholipid.

9. A membrane according to claim 8, wherein the phospholipid is L-α-phosphatidylcholine.

10. A membrane according to claim 8, wherein the phospholipid is present in the form of lipid vesicle liposomes which contain an active agent for delivery to the surface upon which the membrane is disposed in use.

11. A membrane according to claim 10, wherein the active agent for delivery is an antimicrobial compound, a germicide, a steroid, an anaesthetic, a chemotactic agent, an angiogenic agent or an epidermal growth factor.

12. A membrane according to claim 1, further including an emulsifying agent.

13. A membrane according to claim 12, wherein the emulsifying agent is sodium lauryl sulphate.

14. A membrane according to claim 1, further including a plasticizer.

15. A membrane according to claim 14, wherein the plasticizer is glycerol, sorbitol, a propylene glycol, PEG-400, PEG-75-lanolin oil, diethylene glycol, acetylated lanolin or a mixture thereof.

16. A membrane according to claim 1, further including a reinforcing material.

17. A membrane according to claim 16, wherein the reinforcing material is a plastics net or mesh, or a perforated sheet of plastics material.

18. A membrane according to claim 17, wherein the reinforcing material comprises a perforated polyester sheet.

19. A method of treating burns, donor sites, excised wounds, ulcers or dermal abrasions of a non-human patient comprising applying a membrane as claimed in claim 1 to said burn, donor site, wound, ulcer or abrasion.

* * * * *